(12) United States Patent
Potter et al.

(10) Patent No.: US 10,213,565 B2
(45) Date of Patent: Feb. 26, 2019

(54) RESPIRATORY PHYSIOTHERAPY DEVICE

(71) Applicants: Kathryn Potter, Cornubia (AU); Rebecca Houweling, Narangba (AU)

(72) Inventors: Kathryn Potter, Cornubia (AU); Rebecca Houweling, Narangba (AU)

(73) Assignee: HOUWELING POTTER PTY LTD AS TRUSTEE FOR THE HOUWELING ASSET TRUST AND POTTER ASSET TRUST, Bulimba (AU)

( * ) Notice: Subject to any disclaimer, the term of this patent is extended or adjusted under 35 U.S.C. 154(b) by 810 days.

(21) Appl. No.: 14/369,390

(22) PCT Filed: Dec. 18, 2012

(86) PCT No.: PCT/AU2012/001549
§ 371 (c)(1),
(2) Date: Jun. 27, 2014

(87) PCT Pub. No.: WO2013/096988
PCT Pub. Date: Jul. 4, 2013

(65) Prior Publication Data
US 2015/0107595 A1    Apr. 23, 2015

(30) Foreign Application Priority Data

Dec. 31, 2011 (AU) ................. 2011905457

(51) Int. Cl.
*A61M 16/00* (2006.01)
*A63B 23/18* (2006.01)
(Continued)

(52) U.S. Cl.
CPC ........ *A61M 16/0003* (2014.02); *A61M 16/00* (2013.01); *A61M 16/0488* (2013.01);
(Continued)

(58) Field of Classification Search
CPC ...... A61M 16/00; A61M 16/06; A61M 16/08; A61M 16/0003; A61M 16/0006;
(Continued)

(56) References Cited

U.S. PATENT DOCUMENTS 3,491,918 A * 1/1970 Lucas .................... B65D 83/20
                                                    222/635
3,695,608 A * 10/1972 Hanson ................ A61B 5/0875
                                                    446/202
(Continued)

FOREIGN PATENT DOCUMENTS

CH            687296 A5 * 11/1996 ............. A63B 23/18
WO    WO2010129415 A1    11/2010
WO    WO 2011001277 A1 *  1/2011 ............ A61M 16/00

OTHER PUBLICATIONS

International Search Report, dated Apr. 17, 2013.

*Primary Examiner* — Gregory Anderson
*Assistant Examiner* — Margaret Luarca
(74) *Attorney, Agent, or Firm* — Symbus Law Group, LLC; Clifford D. Hyra

(57) ABSTRACT

A device for providing positive expiratory pressure therapy to a patient wherein exhaled air is at a comparatively higher pressure than atmospheric pressure, said device including a container to hold liquid, an air inlet means to allow entry of air into the container and an air outlet to allow air to vent from the container. The air inlet means includes a conduit to discharge the exhaled air. The conduit is fixed in position so that the exhaled air is discharged at or substantially adjacent the base of the container. In use liquid is introduced into the container to a predetermined level and the bottom of the conduit is below the predetermined level of liquid to provide a desired level of positive pressure and the air outlet is above the predetermined level of liquid.

17 Claims, 2 Drawing Sheets

(51) Int. Cl.
    *A61M 16/20*     (2006.01)
    *A63B 21/008*     (2006.01)
    *A63B 21/00*     (2006.01)
    *A61M 16/04*     (2006.01)
    *A61M 16/08*     (2006.01)
    *A63B 71/06*     (2006.01)

(52) U.S. Cl.
    CPC .... *A61M 16/0816* (2013.01); *A61M 16/0875* (2013.01); *A61M 16/20* (2013.01); *A61M 16/208* (2013.01); *A63B 21/00065* (2013.01); *A63B 21/0084* (2013.01); *A63B 23/18* (2013.01); *A61M 2205/21* (2013.01); *A61M 2205/3348* (2013.01); *A61M 2205/3379* (2013.01); *A63B 2071/0694* (2013.01)

(58) Field of Classification Search
    CPC ............ A61M 16/208; A61M 16/0875; A61M 16/816; A61M 16/0488; A61M 16/20; A63B 21/00065; A63B 21/0084; A63B 23/18; B65D 47/20; B65D 43/22; A47G 19/2272

See application file for complete search history.

(56) References Cited

U.S. PATENT DOCUMENTS

| | | | |
|---|---|---|---|
| 3,710,780 A * | 1/1973 | Milch | A63B 23/18 482/13 |
| 3,811,671 A | 5/1974 | Turnbull | |
| 3,869,771 A | 3/1975 | Bollinger | |
| 3,977,399 A | 8/1976 | Brawn | |
| 2009/0056719 A1* | 3/2009 | Newman, Jr. | A61M 16/0666 128/204.18 |
| 2012/0160242 A1* | 6/2012 | Gutierrez Fonseca | A61M 16/00 128/203.26 |

\* cited by examiner

RESPIRATORY PHYSIOTHERAPY DEVICE

This application claims the benefit of Australian patent application No. 2011905457, filed Dec. 31, 2011, which is hereby incorporated by reference in its entirety

FIELD OF INVENTION

The present invention relates to a device for use in physiotherapy. The present invention has particular but not exclusive application for use to improve the lung function of patients

BACKGROUND OF THE INVENTION

Respiratory positive expiratory pressure (PEP) devices are used to assist in exercising patient's lungs and maximising lung function. PEP therapy is desirable for the treatment of conditions affecting respiratory function such as cystic fibrosis, asthma, chronic obstructive pulmonary disease (COPD), and chest infections. Additionally, such therapy is often required following surgery, or during periods of bed rest. These PEP devices provide above atmospheric pressure at the airway when the patient exhales, thus creating resistance. The action of the patient exhaling against the positive pressure exercises the patient's lungs to improve the health of their lungs. Use of PEP therapy promotes reduced air trapping and assists in optimisation of delivery of bronchodilators for the treatment of asthma and COPD. The technique has also been used in the treatment and prevention of atelectasis, and to enhance secretion mobilisation for treatment of cystic fibrosis, chronic bronchitis and bronchiectasis.

PEP devices are generally used in a hospital environment under the direction and guidance of a physiotherapist or other qualified person. However, in certain circumstances it is advantageous for the patient to be able to take the PEP device home to continue treatment once they have been discharged from hospital.

Commercially available respiratory PEP devices are available. Such devices include oscillatory PEP devices which use oscillating steel bearing technology (eg Flutter®, Acapella®). Exhalation by a patient into the valve of an oscillatory PEP device causes a steel ball bearing to oscillate at a high frequency. This results in intermittent positive expiratory pressure and vibration of the patient's airways with the subsequent expectoration of mucus. Devices of this type are generally too expensive for purchase in bulk by a hospital or other organisations. Furthermore, they may be considered too expensive, too fragile or too complicated for use and maintenance by the patient at home.

Bubble positive expiratory pressure devices (Bubble PEPs) have been used by physiotherapists working in the field of cardiorespiratory services. Bubble PEP therapy has been achieved using equipment assembled from a bottle, such as a saline bottle or milk bottle, containing water and a piece of tubing. One end of the length of tubing is inserted into the water, typically at a depth of approximately 10 cm below the water surface. The head of water produces a positive expiratory pressure when the patient exhales through the other end of the tube.

Use of this type of bubble PEP device presents potential hygiene and safety concerns. The current bubble PEP devices cannot be easily and effectively cleaned thus posing contamination risks. There is a risk of aspiration pneumonia or choking occurring if a patient accidentally inhales the liquid into the lungs. Furthermore, the equipment is awkward to use, is not portable and does not produce a reliable or reproducible performance. The resistance produced is inconsistent since there are no markings on the saline or milk bottle to indicate the amount of water necessary to provide the required level of positive pressure. Furthermore the tubing is not easily fixed in place, so the end can move during use causing fluctuations in the level of resistance produced. The equipment is awkward to handle and time consuming to assemble. It can be knocked over easily, and water can be spilled. This form of equipment cannot be readily transferred home with a patient when the patient is discharged from hospital, so is limited to use in the hospital environment. Moreover, use of such devices may be unacceptable in accordance with health related regulations and guidelines.

OBJECT OF THE INVENTION

It is an object of the present invention to provide a physiotherapy device that overcomes at least in part one or more of the abovementioned problems.

SUMMARY OF THE INVENTION

The present invention broadly resides in a device for providing positive expiratory pressure therapy to a patient wherein exhaled air is at a comparatively higher pressure than atmospheric pressure, said device including a container to hold liquid, an air inlet means to allow entry of air into the container and an air outlet to allow air to vent from the container; wherein the air inlet means includes a conduit to discharge the exhaled air, said conduit is fixed in position so that the exhaled air is discharged at or substantially adjacent the base of the container; and wherein in use liquid is introduced into the container to a predetermined level and the bottom of the conduit is below the predetermined level of liquid to provide a desired level of positive pressure and the air outlet is above the predetermined level of liquid.

Preferably the container has a graduated scale to indicate the level of liquid required to be introduced into the container to achieve the desired degree of positive expiratory pressure. Preferably the graduated scale is marked on the container wall.

Preferably the device is a portable, one piece assembly.
Preferably the device can be hand held by the patient.
Preferably the device is adapted to permit easy removal and addition of liquid. In one form there is an opening for addition and removal of liquid. Preferably the container is formed from a plurality of parts. Preferably the container includes a cap and a body. Preferably the cap and body may be sealed together by fastening means. Preferably the device is adapted to be easily dismantled for cleaning. Preferably the cap and body may be sealed together by cooperating screw threads. Alternatively the cap and body may be sealed together using a push fit or a snap fit connection. Preferably the container can accommodate at least a 20 cm head of liquid.

Most preferably the container cap and body are sealed together by a rotatable collar. Preferably the collar has an internal screw thread. Preferably the collar has an aperture adapted to align with the air outlet on the container to allow air to vent from the container when in use. Preferably the collar may be rotated to seal the air outlet to prevent spillage of liquid during transportation and handling. Preferably the collar has an external grip portion to aid in rotating the collar.

Preferably the air inlet means includes a valve to prevent the patient from accidentally inhaling liquid from the container. Preferably the valve is a one-way or non-return, valve, such as a duckbill valve.

Preferably the air inlet means is secured in position to prevent its movement when the respiratory device is in use. Preferably the air inlet means enters the container through an aperture in the container. Preferably the aperture is located in the cap. Preferably the air inlet means cooperates with an aperture in the container cap to prevent movement of the air inlet means during use. Preferably the air inlet means has an annular flange which abuts the internal circumference of the aperture, thus retaining the air inlet means in place to prevent upward movement during use. Preferably the bottom of the conduit contacts the base of the container and cannot move downwards when the patient exhales into the air inlet means. Preferably the bottom of the conduit is beveled to allow air to flow freely from the conduit into the liquid, unhindered by the proximity of the base of the container. Preferably the air inlet means has an internal diameter of at least 8 mm. More preferably the internal diameter is approximately 8 mm.

In use, preferably the patient may exhale directly into the air inlet means. Alternatively the respiratory device may be fitted with an auxiliary mouthpiece or mouthpiece extension in accordance with the needs of the patient.

Preferably the device is adapted to enable it to be used in conjunction with a manometer to measure expiratory pressures.

Preferably the air outlet is located towards the top of the container. Preferably the air outlet has a minimum dimension of approximately 8 mm. Preferably the air outlet is substantially circular, and has a diameter of approximately 8 mm. Preferably the air outlet is adapted to be sealed to prevent spillage or splashing of liquid when handling and transporting the device.

In one form the container is adapted to be held easily by a patient. Preferably the exterior of the container has a recessed section which may assist the patient in holding the device. Preferably the container is substantially cylindrical in shape, and had a recessed cylindrical portion.

In an alternative form the device is fitted with one or more handles. The handles may be adapted to attach to a bed or bed rail, or to be held by the patient.

Preferably the device is made from lightweight, easy to clean materials. Preferably the container is made from plastics. Preferably the container is made from polyethylene terephthalate, polycarbonate, polypropylene, polyvinyl chloride, polystyrene or polyethylene (high density polyethylene or low density polyethylene). More preferably the container is made from high density polyethylene, low density polyethylene or polypropylene. Preferably the device is made from plastics that are substantially free from bisphenol A (BPA).

Preferably the liquid used to provide the positive pressure is water or sterilised water. Alternatively the liquid may be saline solution.

BRIEF DESCRIPTION OF THE DRAWINGS

In order that the present invention can be more readily understood and put into practical effect, reference will now be made to the accompanying drawings wherein.

DETAILED DESCRIPTION OF THE PREFERRED EMBODIMENTS

Figures 1, 2:
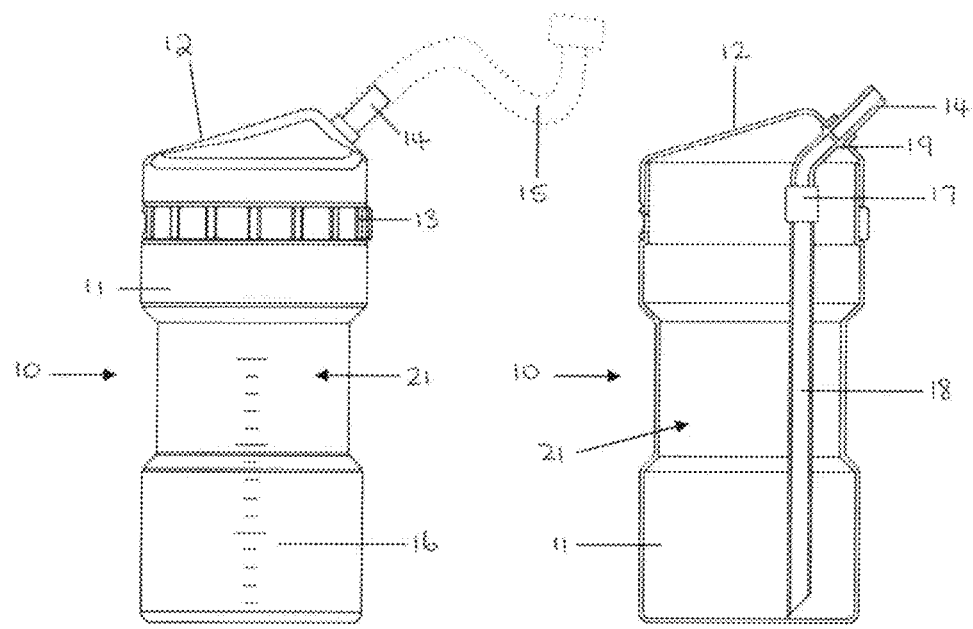
FIG. 1 shows a diagrammatic side view of a preferred embodiment of the respiratory physiotherapy device showing a mouthpiece extension (in phantom)
FIG. 2 is a diagrammatic vertical cross sectional view of the preferred embodiment of FIG. 1.
Figures 3, 4:
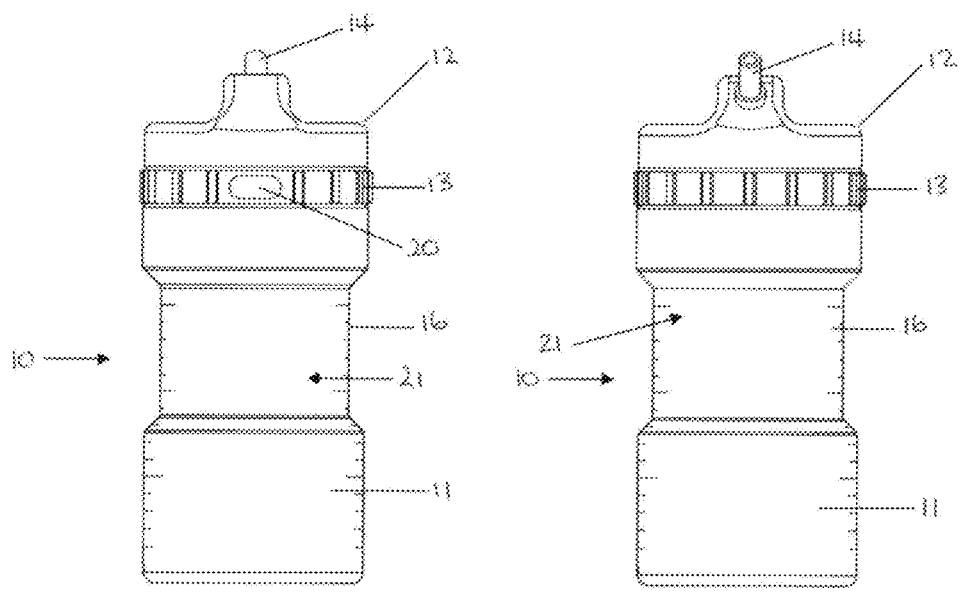
FIG. 3 is a diagrammatic rear view of the preferred embodiment of FIG. 1.
FIG. 4 is a diagrammatic front view of the preferred embodiment of FIG. 1.

With reference to FIGS. 1 to 6 there is shown a respiratory physiotherapy device 10 for use in respiratory therapy according to a first preferred embodiment. The device 10 has a container body 11 for holding liquid, preferably water or sterilised water. The container has a cap 12. The cap 12 has an opening 23 to accommodate an air inlet 14. The air inlet 14 is attached through a valve 17 to a tube 18 which extends downwards substantially to the base of the container 11. The air inlet 14 fits through the opening 23. The air inlet 14 has an annular flange 19 which abuts the internal circumference of the opening 23, thus retaining the air inlet 14, valve 17 and tube 18 in place to prevent upward movement during use. The proximity of the lower end of the tube 18 to the base of the container body 11 prevents the tube 18 from downward movement during use. The exhaled air enters the water at the lower end of the tube 18 near the base of the container 11. The lower end of the tube 18 is beveled to allow air to flow freely from the end of the tube, unhindered by the proximity of the base of the container. The air inlet 14 and tube 18 have an internal diameter of at least 8 mm.

The positive pressure, or resistance level, is set according to the requirements of a particular patient by altering the level of water in accordance with the graduated scale 16 on the container 11 to adjust the resistance in the airway. After water is added to the required level, the resistance provided remains constant during use since the position of the air inlet 14 and tube 18 will not move.

The respiratory device 10 is intended for use during exhalation only. The valve 17 prevents the patient from accidentally inhaling water from the container 11. Such inhalation could otherwise lead to choking, or infection. The valve may suitably be a one-way or non-return valve, such as a duckbill valve.

The container 11 is marked with a graduated scale 16 to indicate the liquid level needed to produce the extent of the resistance required when a patient exhales into the air inlet 14 of the device 10. This ensures that the resistance provided is consistent between therapy sessions, and accurate and meaningful data are recorded, since reference can be made to the scale 16. A typical therapeutic positive expiratory pressure is created by a head of water of 10 cm. However, the head of water may vary depending on the requirements and condition of the patient. The head of water may range from less than 10 cm to 20 cm or more.

The respiratory device 10 has an air outlet 24 located towards the top of the container body 11. The air Outlet 24 allows the exhaled air to vent from the container 11 to prevent a build up of pressure in the device 10. The air outlet 24 is positioned towards the top of the container, and above the maximum liquid level, to prevent spillage or leakage. The air outlet 24 is approximately 8 mm in diameter.

The cap 12 is secured to the container body 11 by a rotating collar 13 with a grip. This collar 13 has an aperture 20 which, on rotation of the collar 13, can be used to seal off the air outlet 24 to prevent spillage of the liquid during transportation, setting up and manipulation of the device 10. In use, the collar 13 must be rotated such that the air outlet 24 and aperture 20 are in alignment with each other to allow the exhaled air to vent from the respiratory device 10 to prevent pressure build up. The collar 13 preferably has an internal screw thread (not shown) to cooperate with corresponding threads on the container body 11 and cap 12.

The container body 11 is substantially cylindrical, and has a recessed cylindrical portion 21 to allow the device to be held easily by the patient.

In use the positive pressure, or resistance level, is set according to the requirements of a particular patient by altering the level of water using the graduated scale 16 on the container body 11. The level of the water corresponds to the amount of resistance in the airway. If the device 10 is held in a constant position during use, the resistance provided by the device 10 to the airways should remain substantially constant.

The patient may use the respiratory device 10 by exhaling directly into the inlet 14. Alternatively, an auxiliary mouthpiece may be used. With particular reference to FIG. 1 there is shown a respiratory physiotherapy device 10 with an extension tube and auxiliary mouthpiece 15 (shown in phantom). The auxiliary mouthpiece 15 is particularly useful if a patient is unable to hold the respiratory device 10, or is bed ridden. In these circumstances the device may be placed on a table or other suitable surface and the mouthpiece 15 can be extended to the patient. The device 10 may be fitted with a holder to store the extension tube and auxiliary mouthpiece.

Figures 5, 6:
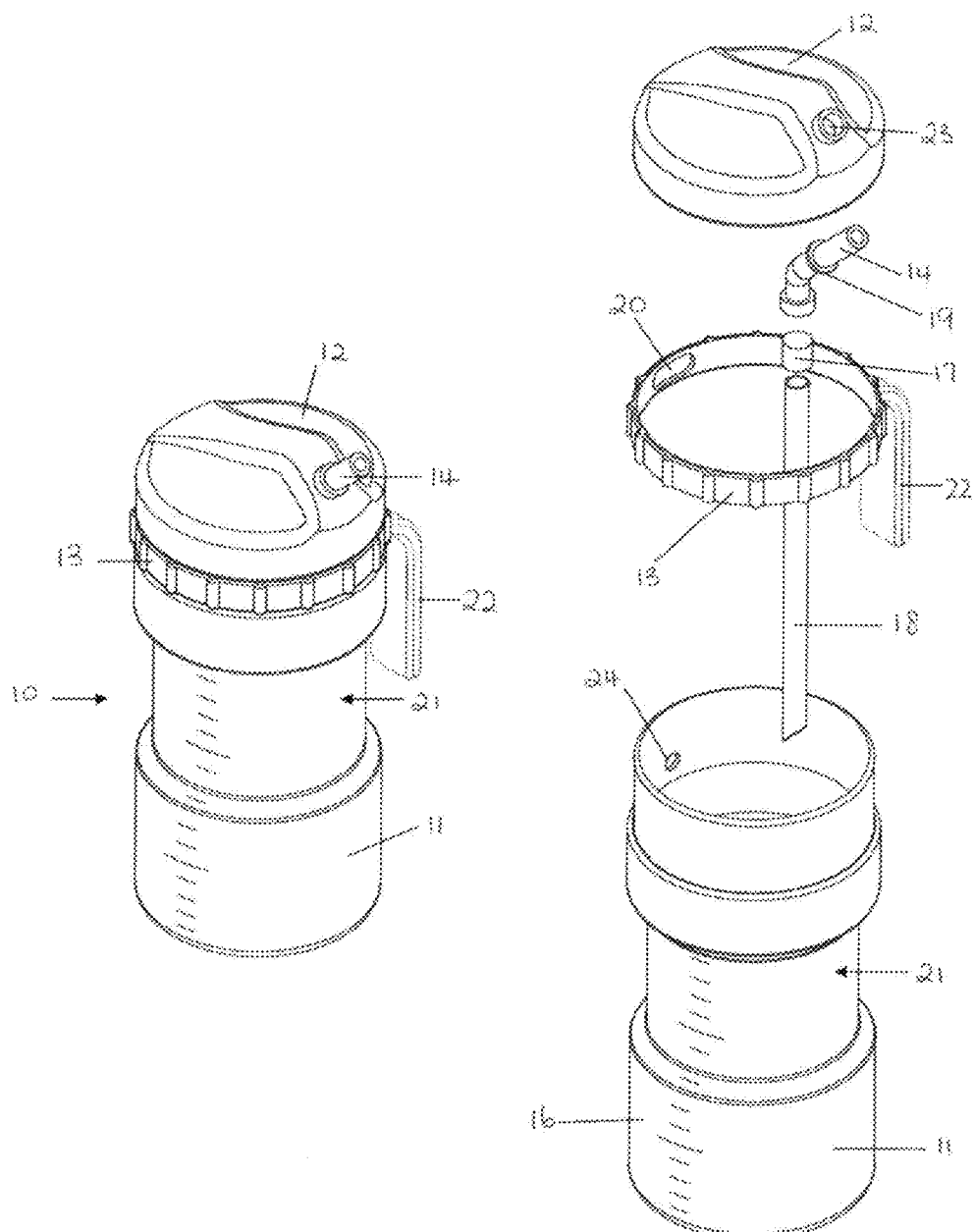
FIG. 5 is a diagrammatic view of the preferred embodiment of the respiratory physiotherapy device showing a handle (in phantom)
FIG. 6 is an exploded view of the preferred embodiment.

The device 10 may be fitted with one or two handles. A handle may be used by the patient to assist in holding the device 10. Alternatively, a handle may be used to attach the device to a bed rail. With particular reference to FIGS. 5 and 6 there is shown a handle 22 (in phantom).

The respiratory device 10 is easily dismantled for cleaning. Suitably it is made of plastic material which is lightweight and easily cleaned such as polyethylene, polypropylene or polyethylene terephthalate. The device may be sterilised, for example in an autoclave.

The respiratory device 10 may be made from coloured material, display illustrations, have the ability to be drawn on or contain coloured liquid to encourage use by children.

The device 10 may be adapted to be used in conjunction with a manometer to measure expiratory pressures. The device may also be adapted to include timing means, such as a digital timer, to assist in timing the length of the expiration phase during therapy.

Advantages

An advantage of the preferred embodiment of the respiratory physiotherapy device is that it is uncomplicated, lightweight and portable. The device is cheap to produce, simple to use, and easy to maintain. In use it forms a one piece apparatus which is easy to handle and manipulate.

The air inlet is in a fixed position, so it cannot move during use. The expired air enters the container at a fixed point near the base of the container, and the resistance level is varied by altering the level of water in accordance with the marked scale on the container.

The resistance provided is also consistent between uses, since reference can be made to the scale on the container wall.

During use constant resistance can be maintained when the patient holds the device in a stable position and preferably consistently flat.

The presence of a one way valve in the inlet avoids risk of inspiration of water by the patient, and removes the risk of choking or infection.

The sealable outlet reduces the risk of spillage of liquid during transportation.

The standardised water level markings reduce risk of inappropriate resistance levels being used for a patient.

The device can be attached to a manometer to verify the expiratory pressure.

The shape of the device allows it to be easily held by the patient. Additional handles provide extra help for certain patients, and allow the device to be attached to a bed rail.

The device is easy to dismantle to allow thorough cleaning, and can be sterilised, leading to improved levels of hygiene.

Although the device is intended primarily for use in hospitals under the guidance of a physiotherapist, the device is simple to use, portable, easy to maintain and cheap to produce making it suitable for use by patients at home after discharge from hospital as a home exercise program for maintenance of lung function. Patients who are being treated in the outpatient setting can also benefit from the use of such a device.

The respiratory physiotherapy device may be brightly coloured, contain coloured water, display illustrations or have the ability to be drawn on or personalised to encourage use by children.

Variations

It will of course be realised that while the foregoing has been given by way of illustrative example of this invention, all such and other modifications and variations thereto as would be apparent to persons skilled in the art are deemed to fall within the broad scope and ambit of this invention as is herein set forth.

Throughout the description and claims of this specification the word "comprise" and variations of that word such as "comprises" and "comprising", are not intended to exclude other additives, components, integers or steps.

The invention claimed is:

1. A portable standalone device to treat a patient using positive expiratory pressure therapy, said device comprising:
    a container adapted to hold a liquid;
    an air inlet adapted to allow entry of air into the container; and
    an air outlet adapted to allow air to vent from the container;
    wherein the air inlet comprises a fixed conduit that has an outlet within the container adapted to discharge exhaled air;
    wherein the container comprises a cap and a body and the container cap and body are sealed together by a rotatable collar and the collar has an aperture adapted to align with the air outlet on the container to allow air to vent from the container when in use;
    wherein the conduit outlet is in a fixed position that does not change based on a level of the liquid within the container and the fixed position is adapted to be below the level of the liquid when the device is in use by the patient;

wherein the level of the liquid within the container determines a level of positive expiratory pressure experienced by the patient when exhaling into the air inlet; and wherein the positive expiratory pressure is changed by changing the level of the liquid in the container with the introduction of additional liquid to the container or removal of a volume of the liquid from the container while the conduit outlet remains in a fixed position irrespective of the liquid level.

2. A device according to claim 1 wherein the air inlet comprises a one way valve to prevent the patient from accidentally inhaling liquid from the container.

3. A device according to claim 1 wherein the conduit extends outside of the container and is secured where the conduit exits the container to prevent its movement when the device is in use.

4. A device according to claim 1 wherein the fixed conduit extends substantially to the base of the container.

5. A device according to claim 1 wherein the conduit outlet is bevelled to allow air to flow freely from the conduit into the liquid.

6. A device according to claim 1 wherein the air outlet on the container is located on the body.

7. A device according to claim 1 further comprising at least one of an auxiliary mouthpiece and a mouthpiece extension, fitted in accordance with needs of the patient.

8. A device according to claim 1 wherein the container comprises a graduated scale to measure the level of the liquid required to achieve the desired positive expiratory pressure.

9. A device according to claim 1 wherein the rotatable collar is adapted to be rotated to seal the air outlet to prevent spillage of liquid during transportation and handling.

10. A device according to claim 1 wherein a portion of the liquid is held by the container and the level of the liquid within the container is such that the level of positive expiratory pressure experienced by the patient is equal to a desired positive expiratory pressure.

11. A method for positive expiratory pressure therapy using the device of claim 1, comprising:

setting a desired positive expiratory pressure by introducing the liquid into the container until the level of positive expiratory pressure reaches the desired positive expiratory pressure.

12. A method according to claim 11, further comprising changing the level of positive expiratory pressure by changing the level of the liquid within the container by introducing additional liquid into the container or removing a volume of the liquid from the container.

13. A method according to claim 11, further comprising exhaling into the air inlet.

14. A method according to claim 11, further comprising aligning the collar aperture with the air outlet on the container to allow air to vent from the container when in use.

15. A method according to claim 11, further comprising rotating the rotatable collar so that the aperture is not aligned with the air outlet, thereby sealing the air outlet to prevent spillage of liquid during transportation and handling.

16. A method according to claim 11, wherein the container comprises a graduated scale to measure the level of the liquid within the container, further comprising measuring the level of the liquid within the container, determining whether the measured level corresponds to the desired positive expiratory pressure, and changing the level of positive expiratory pressure by changing the level of the liquid within the container by introducing additional liquid into the container or removing a volume of the liquid from the container until the measured level corresponds to the desired positive expiratory pressure.

17. A device according to claim 1, wherein the aperture extends all the way through a width of the collar.

* * * * *